US010463462B2

(12) United States Patent
Okai

(10) Patent No.: US 10,463,462 B2
(45) Date of Patent: Nov. 5, 2019

(54) ELECTRIC TOOTHBRUSH APPARATUS

(71) Applicants: COLGATE-PALMOLIVE COMPANY, New York, NY (US); OMRON HEALTHCARE CO., LTD., Kyoto (JP)

(72) Inventor: Takahide Okai, Highland Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 176 days.

(21) Appl. No.: 15/328,579

(22) PCT Filed: Jul. 25, 2014

(86) PCT No.: PCT/US2014/048304
§ 371 (c)(1),
(2) Date: Jan. 24, 2017

(87) PCT Pub. No.: WO2016/014088
PCT Pub. Date: Jan. 28, 2016

(65) Prior Publication Data
US 2017/0216004 A1   Aug. 3, 2017

(51) Int. Cl.
*A46B 17/04* (2006.01)
*A61C 17/22* (2006.01)
(Continued)

(52) U.S. Cl.
CPC .......... *A61C 17/225* (2013.01); *A46B 17/04* (2013.01); *A46B 5/0095* (2013.01); *A46B 9/04* (2013.01); *A61C 17/221* (2013.01); *A61C 17/222* (2013.01)

(58) Field of Classification Search
CPC .............................. A61C 17/225; A46B 17/04
(Continued)

(56) References Cited

U.S. PATENT DOCUMENTS

| 4,408,920 A | 10/1983 | Walther et al. |
| D336,567 S | 6/1993 | Glover et al. |

(Continued)

FOREIGN PATENT DOCUMENTS

| FR | 1063298 A | * 4/1954 | ............. A46B 17/04 |
| GB | 798767 | 7/1958 | |

(Continued)

OTHER PUBLICATIONS

Computer generated English translation of WO 2013/060051 A1, Zhuo, Li, May 2013.*

(Continued)

*Primary Examiner* — Laura C Guidotti

(57) ABSTRACT

An electric toothbrush apparatus including an electric toothbrush handle and a cap coupled thereto for protecting tooth cleaning elements and a user actuatable switch. The electric toothbrush apparatus includes an electric toothbrush handle extending along a handle axis. The electric toothbrush handle comprises a handle portion comprising user actuatable input means, a power source, and a motion inducing assembly. A cap is detachably coupled to the electric toothbrush handle. The cap comprises a tubular sidewall forming a cavity about a cap axis and a protective member axially extending from a bottom edge of the tubular sidewall in a cantilevered manner so as to overly the user actuatable input means to prevent accidental actuation thereof.

18 Claims, 12 Drawing Sheets

(51) Int. Cl.
 *A46B 5/00* (2006.01)
 *A46B 9/04* (2006.01)
(58) Field of Classification Search
 USPC .......................................................... 15/247
 See application file for complete search history.

(56) References Cited

U.S. PATENT DOCUMENTS

| | | | |
|---|---|---|---|
| 5,309,591 | A | 5/1994 | Hagele et al. |
| D493,136 | S | 7/2004 | Since |
| 7,244,073 | B2 | 7/2007 | Trocino |
| D689,697 | S | 9/2013 | Doumoto et al. |
| 9,718,594 | B2 | 8/2017 | Jungnickel et al. |
| 2007/0047620 | A1 | 3/2007 | Lumpkin |
| 2009/0123218 | A1 | 5/2009 | Kim |
| 2011/0061779 | A1 | 3/2011 | Tilgner |
| 2012/0233788 | A1 | 9/2012 | Kitagawa et al. |
| 2013/0000670 | A1 | 1/2013 | Binner et al. |
| 2013/0266362 | A1 | 10/2013 | Curren |
| 2014/0150189 | A1 | 6/2014 | Shigeno et al. |

FOREIGN PATENT DOCUMENTS

| | | |
|---|---|---|
| JP | 2012/075755 | 4/2012 |
| WO | WO 2006/020577 | 2/2006 |
| WO | 2012/109420 | 8/2012 |
| WO | WO 2013/057900 | 4/2013 |
| WO | WO 2013/060051 A1 * 5/2013 ............. A46B 17/04 |
| WO | WO13122297 | 8/2013 |

OTHER PUBLICATIONS

Best China Supplier Sonicare Electric Toothbrush, http://www.alibaba.com/product-detail/Best-China-supplier-sonicare-electric-toothbrush_1494302164.html, downloaded from the internet, date unknown but prior to Jul. 25, 2014.

Panasonic EW-DS90-K, http://www.amazon.com/Panasonic-EW-DS90-K-Compact-Battery-Powered-Toothbrush/dp/B0090JS6Z8/ref=sr_1_1?ie=UTF8&qid=1393453602&sr=8-1&keywords=Panasonic+Adult+Portable+Compact+Toothbrush, downloaded from the internet, date unknown but prior to Jul. 25, 2014.

Soelu Electric toothbrush, http://global.rakuten.com/en/store/okuchi/item/i-00001079/, downloaded from the internet, date unknown but prior to Jul. 25, 2014.

Travel Portable Colorful Electric Toothbrush, http://www.dhgate.com/product/4pcs-iot-travel-portable-colorful-electric/143244625.html, downloaded from the internet, date unknown but prior to Jul. 25, 2014.

International Search Report and the Written Opinion of the International Searching Authority issued in international application PCT/US2014/048304 dated Jun. 23, 2015.

* cited by examiner

ELECTRIC TOOTHBRUSH APPARATUS

BACKGROUND

Powered or electric toothbrushes having replaceable heads, commonly referred to as refill heads, are known in the art. Such powered toothbrushes typically include a handle and a refill head that is detachably coupled to the handle. These powered toothbrushes also typically include a power switch that enables a user to power the toothbrush on and off for supplying movement to the refill head. It is often desirable to protect the bristles of the refill head from damage to prolong the life cycle of the refill head. Furthermore, it may be desirable to protect the power switch against accidental activation. Such protection devices that are currently known are bulky and enclose the entire electric toothbrush, thereby increasing manufacturing costs and creating an undesirable aesthetic. Thus, a need exists for an improved electric toothbrush apparatus that includes a protection device for protecting both the bristles of the refill head and the power switch.

BRIEF SUMMARY

The present invention is directed to an electric toothbrush apparatus that includes an electric toothbrush handle that includes a handle portion and a stem portion. The handle portion may include a user actuatable power switch. The electric toothbrush apparatus also includes a cap. The cap has a cavity within which the stem portion of the electric toothbrush handle is disposed when the cap is coupled to the electric toothbrush. The cap also has a protective member that may overlie the user actuatable power switch.

In one embodiment, the invention can be an electric toothbrush apparatus comprising: an electric toothbrush handle extending along a handle axis, the electric toothbrush handle comprising: a handle portion comprising a user actuatable power switch; a stem portion axially protruding from the handle portion, the stem portion configured to couple a replaceable toothbrush head to the electric toothbrush handle; a power source; and a motion inducing assembly; a cap comprising: a tubular sidewall forming a cavity about a cap axis, the cavity having an open bottom end; and a protective member axially extending from a bottom edge of the tubular sidewall in a cantilevered manner; and the cap detachably coupled to the electric toothbrush so as to be alterable between: (1) a protective state in which the cap is mounted to the electric toothbrush such that the stem portion is located within the cavity and the protective member overlies the user actuatable power switch; and (2) a use state in which the cap is removed from the electric toothbrush handle.

In another embodiment, the invention can be an electric toothbrush apparatus comprising: an electric toothbrush handle extending along a handle axis, the electric toothbrush handle comprising: a handle portion comprising user actuatable input means; a toothbrush head coupled to the electric toothbrush handle; a power source; and a motion inducing assembly; a cap detachably coupled to the electric toothbrush handle, the cap comprising: a tubular sidewall forming a cavity about a cap axis, the cavity having an open bottom end, the toothbrush head located within the cavity; and a protective member axially extending from a bottom edge of the tubular sidewall in a cantilevered manner, the protective member overlying the user actuatable input means to prevent actuation thereof.

In yet another embodiment, the invention can be an electric toothbrush apparatus comprising: an electric toothbrush handle extending along a handle axis, the electric toothbrush handle comprising: a handle portion comprising user actuatable input means; a toothbrush head having cleaning elements thereon coupled to the handle portion; a power source; and a motion inducing assembly; a cap detachably coupled to the electric toothbrush handle, the cap comprising: a sidewall having an inner surface that forms a cavity having an open bottom end and a closed top end, the toothbrush head positioned within the cavity; and a hole forming a first passageway from an ambient atmosphere to a top portion of the cavity; and a second passageway extending from the ambient atmosphere to a bottom portion of the cavity.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
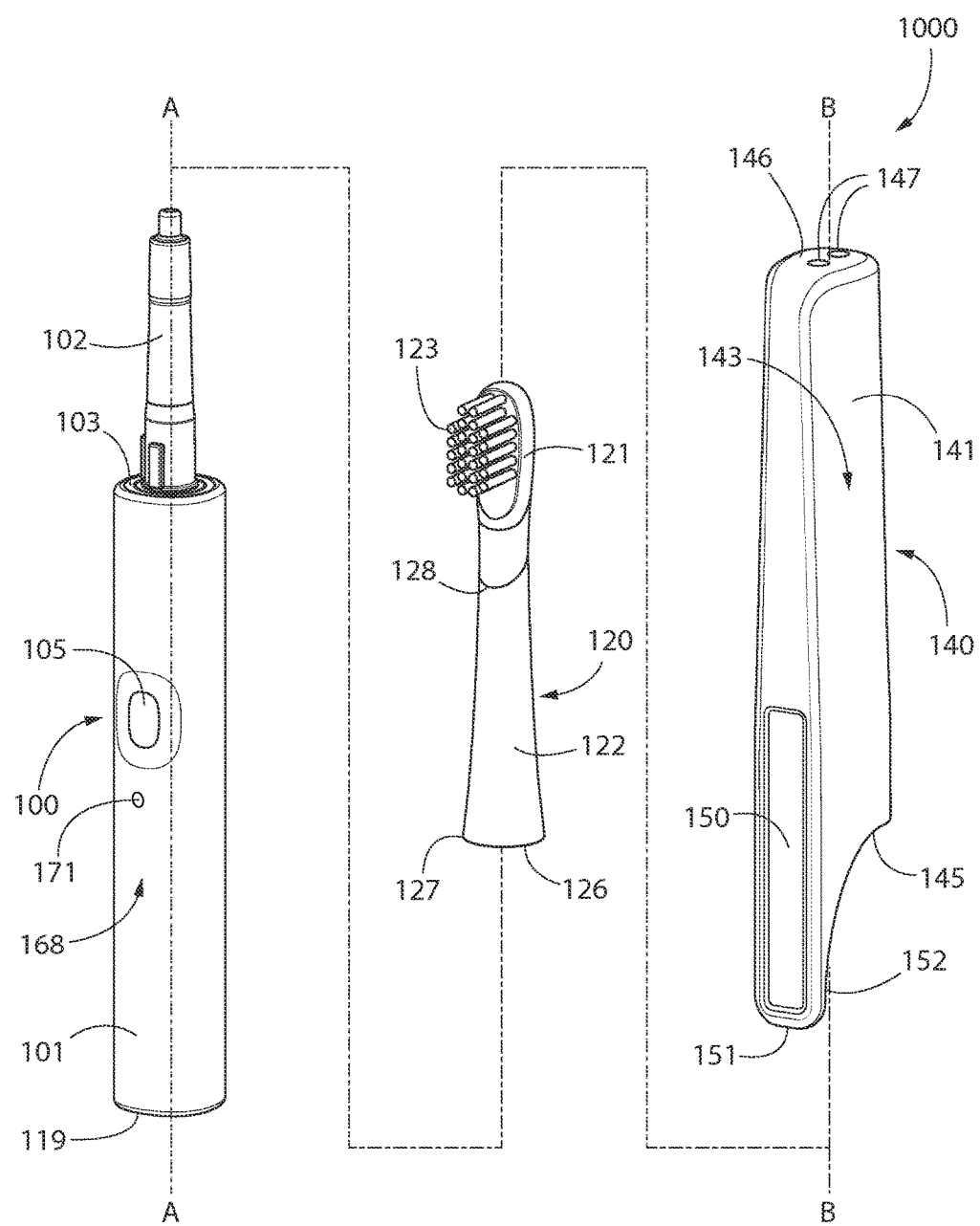
FIG. 1 is a front perspective view of an electric toothbrush apparatus including an electric toothbrush handle, a toothbrush head and a cap in an exploded state in accordance with a first embodiment of the present invention.

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Figure 2:
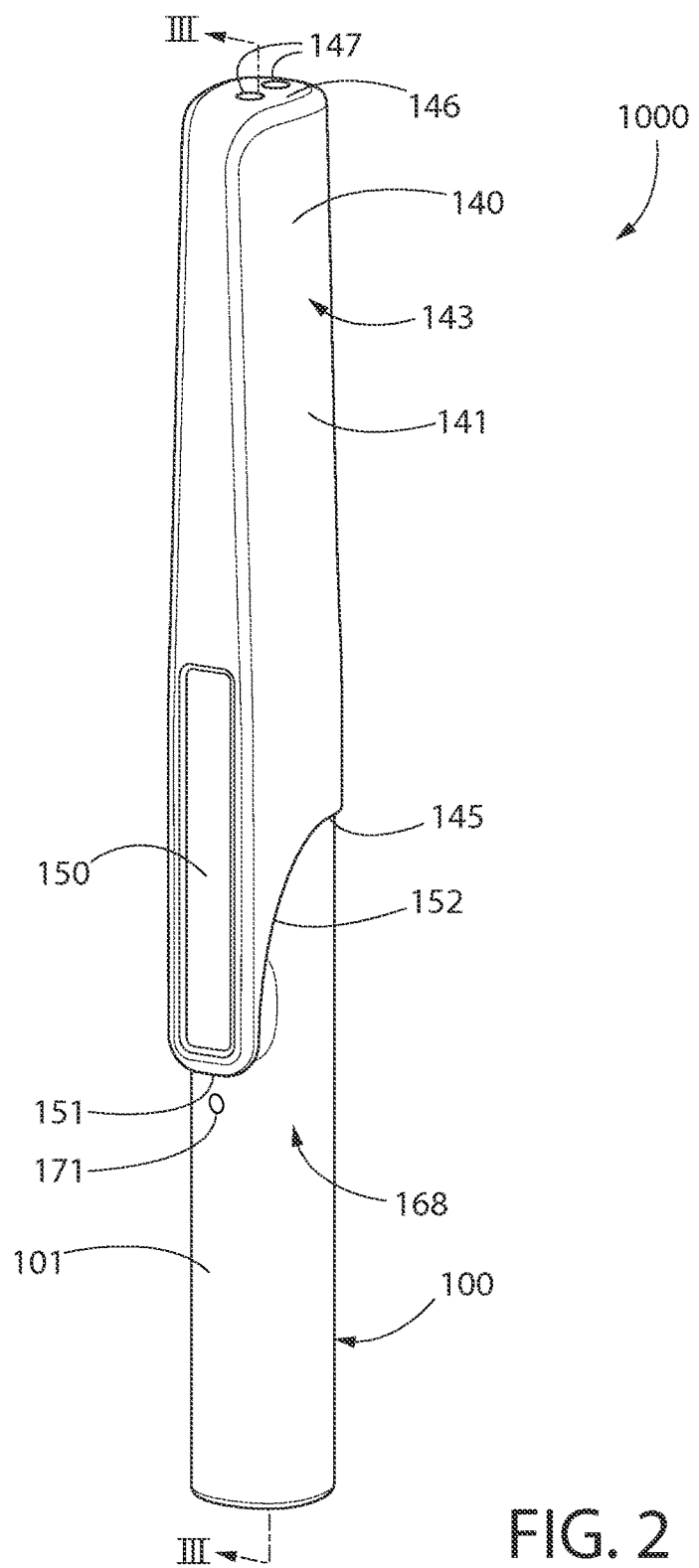
FIG. 2 is front perspective view of the electric toothbrush apparatus of FIG. 1 in an assembled state.
Figure 3:
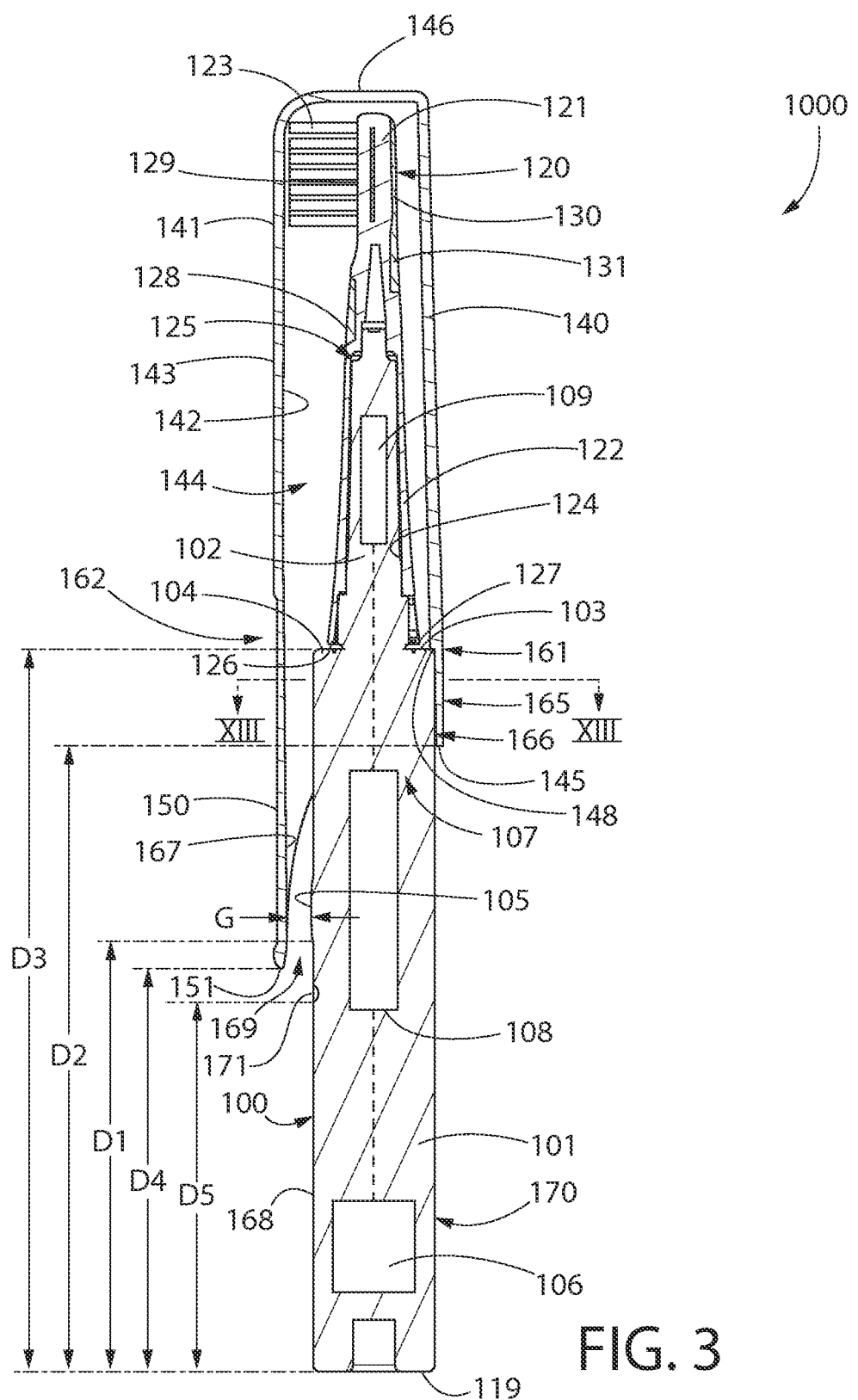
FIG. 3 is a cross-sectional view taken along line III-III of FIG. 2.
Figure 4:
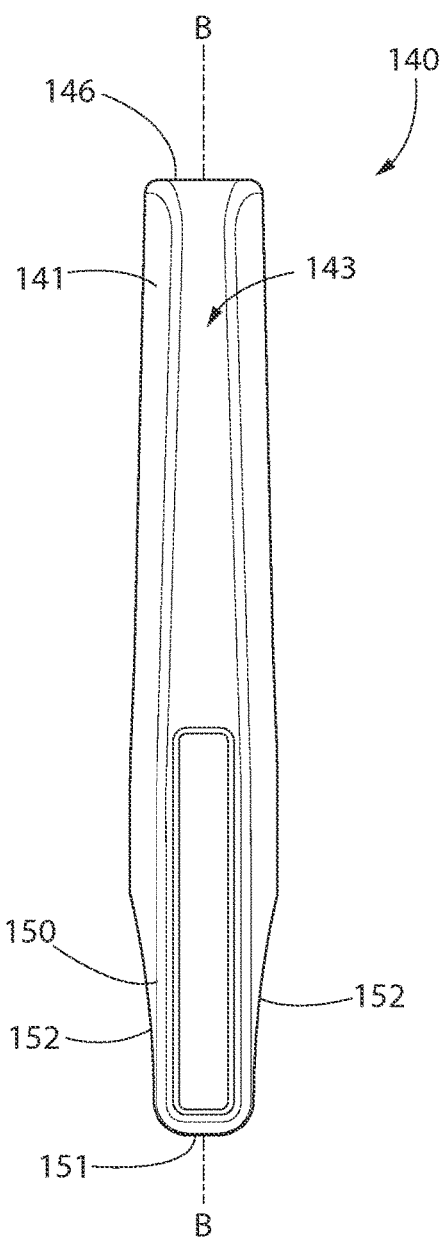
FIG. 4 is a front view of the cap of the electric toothbrush apparatus of FIG. 1.
Figure 5:
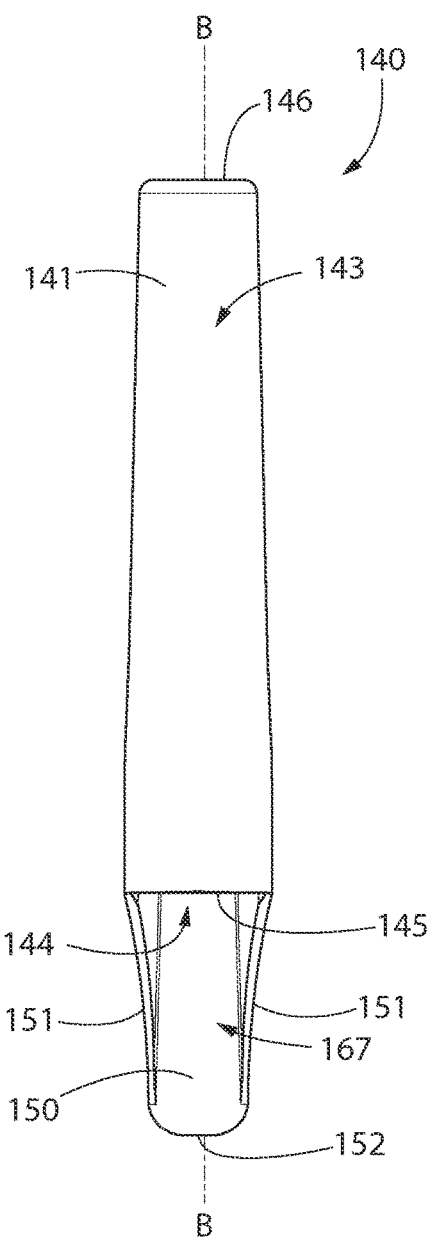
FIG. 5 is a rear view of the cap of FIG. 4.
Figure 6:
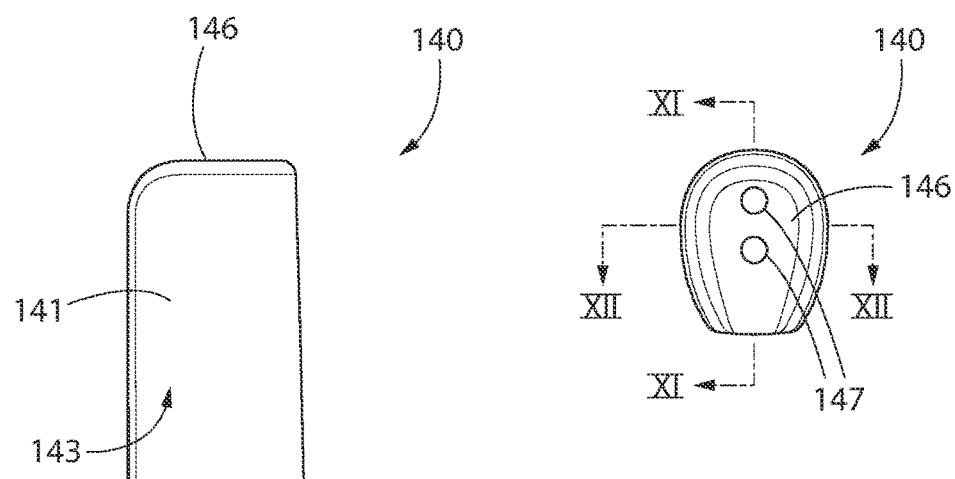
FIG. 6 is a left-side view of the cap of FIG. 4, the right-side view being a mirror image thereof.
Figure 7:
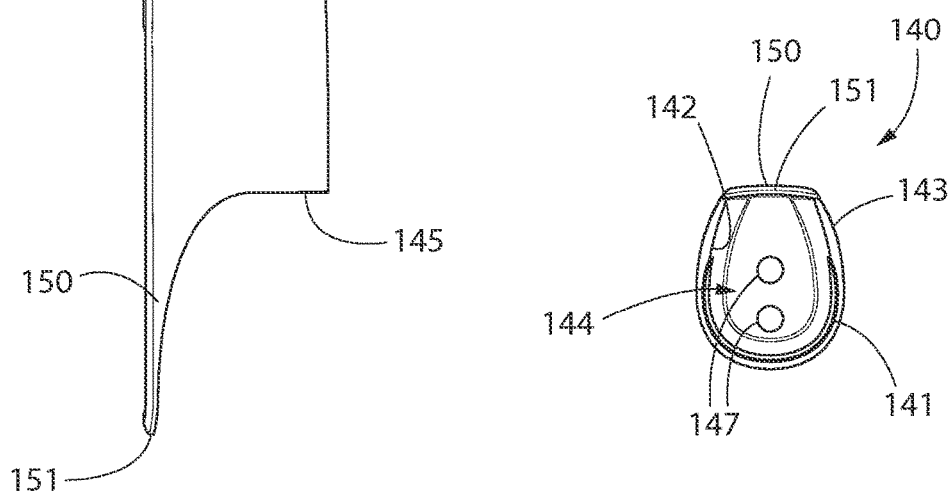
FIG. 7 is a top view of the cap of FIG. 4.
Figure 8:
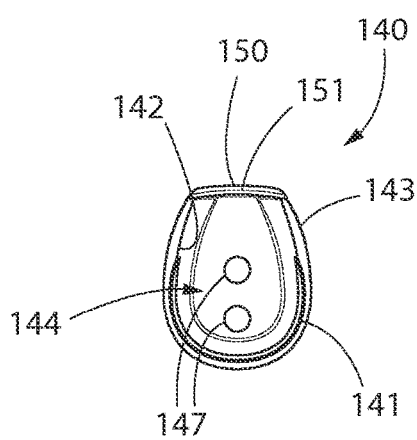
FIG. 8 is a bottom view of the cap of FIG. 4.
Figures 9, 10:
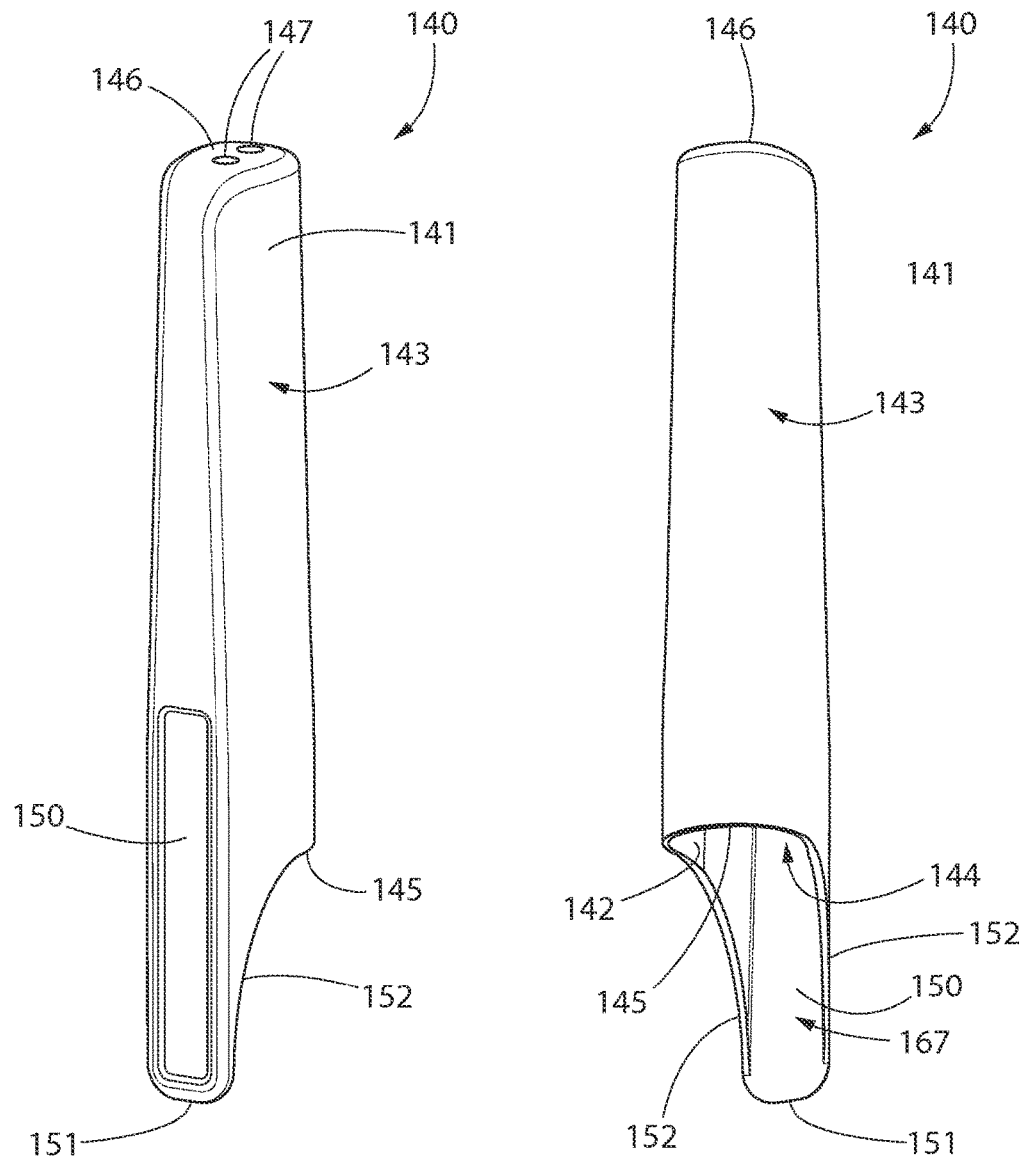
FIG. 9 is a front perspective view of the cap of FIG. 4.
FIG. 10 is a rear perspective view of the cap of FIG. 4.
Figures 11, 12:
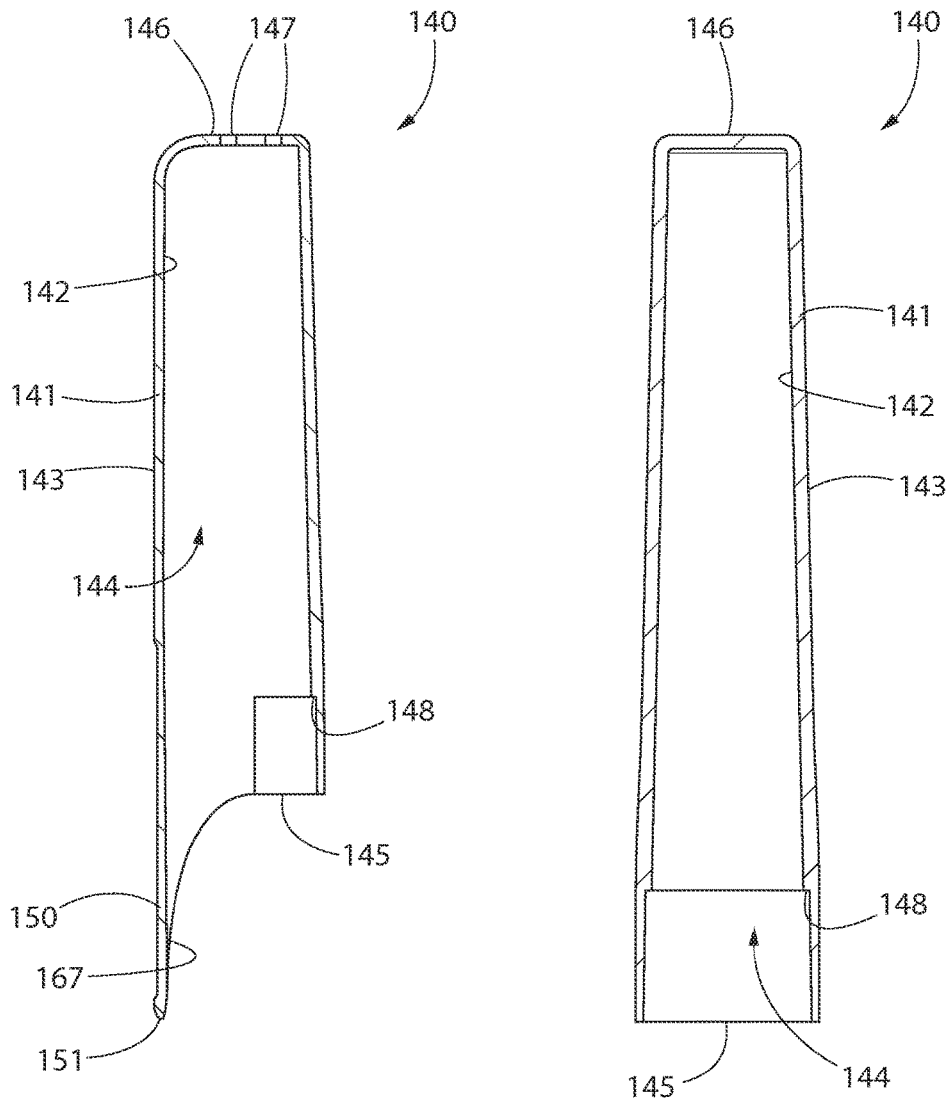
FIG. 11 is a cross-sectional view taken along line XI-XI of FIG. 7.
FIG. 12 is a cross-sectional view taken along line XII-XII of FIG. 7.

Referring first to FIGS. 1 through 3 concurrently, an electric toothbrush apparatus 1000 will be described in accordance with one embodiment of the present invention. The electric toothbrush apparatus 1000 generally comprises an electric toothbrush handle 100, a toothbrush head 120 and a cap 140. In the exemplified embodiment, the electric toothbrush handle 100 generally includes a handle portion 101 and a stem portion 102, the details of which will be discussed in more detail below.

In the exemplified embodiment, the toothbrush head 120 is a replaceable toothbrush head, also known in the art as a refill head. The toothbrush head 120 and the electric toothbrush handle 100 are designed so that the toothbrush head 120 can be repetitively coupled to and decoupled from the electric toothbrush handle 100. In FIG. 1, the electric toothbrush apparatus 1000 is illustrated in a state wherein the toothbrush head 120 is not coupled to the electric toothbrush handle 100 and in FIGS. 2 and 3 the electric toothbrush apparatus 1000 is illustrated in a state wherein the toothbrush head 120 is detachably coupled to the electric toothbrush handle 100. The toothbrush head 120 may be detachably coupled to the electric toothbrush handle 100 using any means known in the art, such as including without limitation snap-fit, friction fit, interference fit, tongue and groove, protrusion and recess, fasteners or the like. Typically, the toothbrush head 120 is non-rotatable relative to the electric toothbrush handle 100 when coupled thereto so that the toothbrush head 120 does not rotate relative to the electric toothbrush handle 100 during use.

While the invention is exemplified herein as an electric toothbrush apparatus, it is to be understood that the inventive concepts discussed herein can be applied to manual toothbrushes that utilize refill heads, or other manual or powered oral care implements, including without limitation tongue cleaners, water picks, interdental devices, tooth polishers and specially designed ansate implements having tooth engaging elements. Specifically, in one embodiment the inventive concepts discussed herein can be applied to any of the above-noted implements when the implement includes a user actuatable power switch or input means for providing some function to the implement, as discussed in more detail below.

The toothbrush head 120 generally comprises a head portion 121 and a sleeve portion 122. The head portion 121 and the sleeve portion 122 can be formed of a material that is rigid, such as a moldable hard plastic. Suitable hard plastics include polymers and copolymers of ethylene, propylene, butadiene, vinyl compounds and polyesters such as polyethylene terephthalate. Of course, the invention is not to be so limited and other materials can be used to form the sleeve portion 122 and the head portion 121 of the toothbrush head 120.

In the exemplified embodiment, the sleeve portion 122 and the head portion 121 of the toothbrush head 120 are integrally formed as a single unitary structure using a molding, milling, machining or other suitable process. However, in other embodiments the head portion 121 and the sleeve portion 122 of the toothbrush head 120 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners.

The head portion 121 comprises a plurality of tooth cleaning elements 123 extending from a surface thereof as is known in the art. In the exemplified embodiment, the plurality of tooth cleaning elements 123 extend from a front surface 129 of the head portion 121. Furthermore, although the head portion 121 has been described above as being formed from a rigid material such as a molded hard plastic, the head portion 121 may also include portions that are formed of a thermoplastic elastomer or other rubber material. Specifically, the head portion 121 may include a soft tissue cleaner 131 on its rear surface 130 for massaging of a user's soft tissue surface and tongue. Such a soft tissue cleaner 131 may include nubs, ridges and/or depressions for facilitating removal of contaminants from a user's tongue and other tissue surfaces. The head portion 121 may have other regions that include a thermoplastic elastomer type material as desired to enhance user comfort, flexibility of the head portion 121 and cleaning efficiency or effectiveness.

The plurality of tooth cleaning elements 123 are provided for cleaning and/or polishing an oral surface and/or interdental spaces. The tooth cleaning elements 123 can be particularly suited for brushing teeth, or can be particularly suited to polish teeth instead of or in addition to cleaning teeth. As used herein, the term "tooth cleaning elements" is used in a generic sense to refer to any structure that can be used to clean, polish or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth cleaning elements 123 of the present invention can be connected to the toothbrush head 120 in any manner known in the art. For example, staples/anchors, in-mold tufting (IMT) or anchor free tufting (AFT) could be used to mount the tooth cleaning elements/tooth engaging elements. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

The sleeve portion 122 of the toothbrush head 120 extends from a proximal end 127 to a distal end 128. The head portion 121 of the toothbrush head 120 is coupled to the distal end 128 of the sleeve portion 122. Furthermore, the sleeve portion 122 comprises an inner surface 124 that forms a sleeve cavity 125. The sleeve cavity 125 has an open bottom end 126 at the proximal end 127 of the sleeve portion 122. The sleeve cavity 125 is sized and shaped to accommodate the stem portion 102 of the electric toothbrush handle 100 so that the toothbrush head 120 can be detachably coupled to the electric toothbrush handle 100 as described below. Specifically, the open bottom end 126 of the sleeve portion 122 provides a passageway into the sleeve cavity 125 so that the stem portion 102 of the electric toothbrush handle 100 can be axially translated into and out of the cavity 182 via the opening 123.

The electric toothbrush handle 100 extends along a handle axis A-A. Conceptually, the handle axis A-A is a reference line that is generally coextensive with the three-dimensional center line of the electric toothbrush handle 100. Because the electric toothbrush handle 100 may, in certain embodiments, be a non-linear structure, the handle axis A-A of the electric toothbrush handle 100 may also be non-linear in certain embodiments. However, the invention is not to be so limited in all embodiments and in certain other embodiments the electric toothbrush handle 100 may have a simple linear arrangement and thus a substantially linear handle axis A-A.

As noted above, the electric toothbrush handle 100 generally includes a handle portion 101 and a stem portion 102. In certain embodiments, the handle portion 101 and the stem portion 102 are integrally formed as a single unitary structure using a molding, milling, machining or other suitable process. However, in other embodiments the handle portion 101 and the stem portion 102 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners.

The handle portion 101 has a top end 103 and a bottom end 119, and the stem portion 102 axially protrudes from the top end 103 of the handle portion 101 in the direction of the handle axis A-A. Furthermore, the top end 103 of the handle portion 101 comprises or forms a transverse step 104. The stem portion 102 is the portion of the electric toothbrush handle 100 that is configured to couple with the toothbrush head 120 to form the assembled electric toothbrush apparatus 1000 (see FIG. 3). In the exemplified embodiment, the stem portion 102 and the handle portion 101 are both aligned along the handle axis A-A. However, in other embodiments the stem portion 102 may extend from the top end 103 of the handle portion 101 so as to be offset from the handle axis A-A.

The handle portion 101 of the electric toothbrush handle 100 is an elongated structure that provides the mechanism by which the user can hold and manipulate the electric toothbrush apparatus 1000 during use. The handle portion 101 can take on a wide variety of shapes, contours and configurations, none of which are limiting of the present invention. In the exemplified embodiment, the handle portion 101 is tubular or cylindrical in shape and has a constant outer diameter. In other embodiments the outer diameter of the handle portion 101 may change along the length of the handle portion 101 to achieve a desired gripping comfort. Furthermore, in certain embodiments the outer surface of the handle portion 101 may be partially or entirely coated or covered with an elastomeric material to increase gripability and comfort to a user during use of the electric toothbrush apparatus 100.

In the exemplified embodiment, the handle portion 101 of the electric toothbrush handle 100 comprises a user actuatable power switch 105 that controls the various operations of the toothbrush 1000, including without limitation turning or powering the electric toothbrush apparatus 100 off and on, changing speeds of the motor, changing the color of an illumination device, changing an output such as a song, a hum or any other sound being emitted from the electric toothbrush apparatus 1000 or other included functions. In the exemplified embodiment, the handle portion 101 of the electric toothbrush handle 100 may also include a status indicator element 171 such as, for example but not limited to, an LED or other visible light-producing device to indicate one or more states of the electric toothbrush apparatus 1000 such as power on, power off, battery charging, battery power low, operation mode, motor speed, etc. The status indicator element 171 may be provided on an outer surface of the handle portion 101 such as, for example, adjacent to the power switch 105, for example between the power switch 105 and the bottom end 119 of the handle portion 101. In certain embodiments, the handle portion 101 is a hollow structure having an interior cavity within which the electrical circuitry and mechanical components of the electric toothbrush apparatus 1000 are provided. In such embodiments, the handle portion 101 forms a watertight housing for any electrical circuit and mechanical components that need to be protected from moisture.

In the exemplified embodiment, the user actuatable power switch 105 is a depressible button switch. However, the invention is not to be so limited and in certain other embodiments the user actuatable power switch 105 may be a slide switch, multiple buttons, a capacitance switch (i.e., a touch switch) such as one that closes when in contact with a user's hand, or the like. Alternatively, the user actuatable power switch 105 may be a display, such as one that includes a touch screen that enables user control through simple or multi-touch gestures by touching the screen of the display with a stylus or one or more of the user's fingers. In certain embodiments, the user actuatable power switch 105 can be any structural component that facilitates powering on and off the electric toothbrush apparatus 1000 or control of other functions of the electric toothbrush apparatus 1000. Furthermore, in certain embodiments the user actuatable power switch 105 may be considered a user actuatable input means such that the user actuatable power switch 105 can be any structure that permits a user to input instructions to the electric toothbrush apparatus 1000, including instructions related to any of the device functions noted above. A button switch or any of the other devices noted above can be considered a user actuatable input means.

The electric toothbrush handle 100 also comprises a power source 106 and a motion inducing assembly 107. The power source 106 may be one or more batteries, such as rechargeable or disposable batteries, a DC or AC power supply (i.e., a power cord that is capable of being plugged into a wall or other device), or any other source that is able to provide power to the motion inducing assembly 107. In the exemplified embodiment, the motion inducing assembly 107 comprises a drive assembly 108 and an eccentric 109. The power source 106, the drive assembly 108 and the eccentric 109 are generically depicted as a rectangular box in FIG. 3, it being understand that the specific structure of these components can take on any of a variety of shapes, sizes, orientations or the like.

In the exemplified embodiment the power source 106 and the drive assembly 108 are located within the handle portion 101 and the eccentric 109 is located within the stem portion 102. Of course, the power source 106 and drive assembly 108 could alternatively be located within the stem portion 102 and the eccentric 109 could alternatively be located within the handle portion 101 in other embodiments. The drive assembly 108 may include a motor and a drive train, such as a variety of gears and the like, that couple the motor to the eccentric 109. In other embodiments, the motor may be coupled directly to the eccentric 109. The drive assembly 108 is operably coupled to the power source 106 so that upon powering on the power source 106, such as by actuating the user actuatable power switch 105, the drive assembly 108 is powered on and the motor begins rotating. Operation of the drive assembly 108 and rotation of the motor is imparted to the tooth cleaning elements 123 of the toothbrush head 120 so that the tooth cleaning elements 123 are movable (actual movement by location change or vibrational movement) relative to the remainder of the toothbrush head 120 to facilitate an enhanced cleaning effect.

In one embodiment, movement can be imparted to the tooth cleaning elements 123 as follows. The eccentric 109 can be operably coupled to the drive assembly 108, such as to a drive shaft of the motor. As the motor rotates when it is powered, the drive shaft also rotates. As the drive shaft rotates, the eccentric 109, which has an off-center center of gravity, generates vibrations that are transmitted to the toothbrush head 120. Thus, in such an embodiment the movement of the tooth cleaning elements 123 is vibrational movement. The eccentric 109 may be formed as a portion of a drive shaft that is radially offset from a longitudinal axis of the drive shaft, or the eccentric 109 may be an offset disc or other offset weight. Additional details of a suitable vibratory producing handle, and related structure that can be incorporated into the electric toothbrush apparatus 1000 of the present invention, can be found in U.S. Patent Application Publication No. 2010/0269275, Shimoyama et al., published Oct. 28, 2010 (filed as U.S. patent application Ser. No. 12/377,355), the entirety of which is hereby incorporated by reference.

In other embodiments the motor and drive shaft may be coupled directly to a cleaning element carrier that is movably coupled to the toothbrush head 120. Movement of the motor and drive shaft may result in the cleaning element carrier moving in a rotational direction, oscillating back and forth in a rotational or linear direction, or moving in any other desired direction. Thus, the movement of the tooth cleaning elements 123 can be achieved by using an eccentric or a movable cleaning element carrier, or by any other means known in the art, and various modifications of the manner of movement of the tooth cleaning elements 123 are possible in the inventive electric toothbrush apparatus 1000.

Referring now to FIGS. 1-12 concurrently, the cap 140 of the electric toothbrush apparatus 1000 and its relationship with the electric toothbrush handle 100 when coupled thereto will be described. The cap 140 generally comprises a tubular sidewall 141 having an inner surface 142 and an outer surface 143. Although described herein as being tubular, in other embodiments the sidewall 141 can take on other shapes and need not be tubular in all embodiments. The inner surface 142 of the tubular sidewall 141 at least partially defines and surrounds a cavity 144. More specifically, the tubular sidewall 141 forms the cavity 144 about a cap axis B-B. The tubular sidewall 141 extends along the cap axis B-B from a bottom edge 145 to an upper wall 146. The bottom edge 145 defines an opening through which the electric toothbrush handle 100 can be inserted when it is desired to couple the cap 140 to the electric toothbrush handle 100 as discussed below. Furthermore, the upper wall 146 encloses a top end of the cavity 144.

The cap 140 may be formed of a rigid material, such as any one of the moldable hard plastic materials discussed above. Of course, the invention is not to be so limited in all embodiments and in certain other embodiments the cap 140 may be formed of other materials, including metals and metal alloys, rubber, thermoplastic elastomers, or the like. Furthermore, in certain embodiments the cap 140 may be formed of a transparent material. In other embodiments the cap 140 may be formed of a translucent material, such as a material of a particular color that can be seen through but not without some distortion or loss of detail. In still other embodiments the cap 140 may be formed of an opaque material so that the cap 140 cannot be seen through.

The cap 140 is detachably couplable to the electric toothbrush handle 100. More specifically, the cap 140 is detachably couplable to the electric toothbrush handle 100 so as to be alterable between: (1) a protective state in which the cap 140 is mounted to the electric toothbrush handle 100 such that the stem portion 102 of the electric toothbrush handle 100 is located within the cavity 143 of the cap 140 (FIGS. 2 and 3); and (2) a use state in which the cap 140 is removed from the electric toothbrush handle 100. Although described above wherein the cap 140 is coupled to the electric toothbrush handle 101, the invention is not to be so limited and the cap 140 may be considered to be coupled to the electric toothbrush apparatus 1000, or more specifically to one of the electric toothbrush handle 100 (either or both of the handle portion 101 and the stem portion 102) or the toothbrush head 120.

In the exemplified embodiment, one or more holes 147 are formed into the upper wall 146 of the cap 140 for venting the cavity 144 when the cap 140 is in the protective state and coupled to the electric toothbrush handle 100. Each of the holes 147 forms a passageway from the ambient atmosphere outside of the electric toothbrush apparatus 1000 to a top portion of the cavity 144. Although the holes 147 are illustrated as being formed into the upper wall 146 of the cap 140 in the exemplified embodiment, the invention is not to be so limited and in other embodiments the holes 147 may be formed into the tubular sidewall 141 of the cap 140. In the exemplified embodiment, the cap 140 includes two of the holes 147, although a single hole or more than two holes may be used in other embodiments. Furthermore, holes may be provided on both of the upper wall 146 and sidewall 141 of the cap 140 in some embodiments.

In addition to the tubular sidewall 141, in the exemplified embodiment the cap 140 also comprises a protective member 150 that extends axially from the bottom edge 145 of the tubular sidewall 141 in a direction away from the bottom edge 145 and away from the upper wall 146. In the exemplified embodiment, the protective member 150 extends from the bottom edge 145 of the tubular sidewall 141 in a cantilevered manner. The protective member 150 terminates in a free end 151. The protective member 150, in the exemplified embodiment, comprises a flat plate 154 and first and second sidewalls 152 extending from a rear surface of the flat plate 154. The first and second sidewalls 152 are non-coplanar with the flat plate 154 and extend from the bottom edge 145 of the tubular sidewall 141, thereby providing additional rigidity to the protective member 150. In the exemplified embodiment, the first and second sidewalls 152 do not extend along the entire axial length of the protective member 150. In other embodiments, however, the first and second sidewalls 152 may extend the entire length of the protective member 150 and may even form a portion of the free end 151. In such an embodiment, the protective member 150 may have a generally U-shaped or semi-oval cross-section.

In the exemplified embodiment, the protective member 150 extends from the tubular sidewall 141 in a cantilevered manner and, thus, can be considered as a separate component than the tubular sidewall 141. In other embodiments in which the focus is on the improved venting capabilities of the cap 140, the protective member 150 may simply be a portion of the tubular sidewall 141. In one such embodiment, the bottom edge 145 of the tubular sidewall 141 may be an annular edge.

The inner surface 142 of the tubular sidewall 141 comprises a transverse shoulder 148. When the cap 140 is in the protective state as illustrated in FIG. 3, the transverse shoulder 148 of the tubular sidewall 141 abuts the transverse step 104 of the handle portion 101. More specifically, the transverse shoulder 148 of the tubular sidewall 141 is in surface contact with the transverse step 104 of the handle portion 101. As can be seen in FIG. 3, a first portion 161 of the cap 140 is in contact with the transverse step 104 of the handle portion 101 and a second portion 162 of the cap 140 is spaced apart from and not in contact with the transverse step 104 of the handle portion 101. Specifically, in the exemplified embodiment only the portion of the transverse step 104 on a rear of the electric toothbrush apparatus 1000 is abutted by the transverse shoulder 148 of the tubular sidewall 141 and the portion of the transverse step 104 on a front of the electric toothbrush apparatus 1000 is not in contact with the transverse shoulder 148 of the tubular sidewall 141. Of course, the invention is not to be so limited in all embodiments and in certain other embodiments the transverse shoulder 148 may abut the transverse step 104 around the entire circumference of the handle portion 101. In such an embodiment the abutment between the transverse shoulder 148 and the transverse step 104 may completely seal the cavity 144 to protect the toothbrush head 120 and to provide a water resistant layer for the toothbrush head 120.

Referring now to FIG. 3, the cap 140 is illustrated in the protective state such that the cap 140 is coupled or mounted to the electric toothbrush handle 120. When in the protective state, the toothbrush head 120 including the tooth cleaning elements 123 are disposed within the cavity 144 of the cap 140. Furthermore, the protective member 150 of the cap 140 is positioned so as to overlie the user actuatable power switch 105. Stated another way, any transverse plane that is perpendicular to the handle axis A-A and that intersects the user actuatable power switch 105 will also intersect the protective member 150 of the cap 140. Thus the protective member 150 of the cap 140 serves to protect the user actuatable power switch 105 against accidental actuation or damage.

The user actuatable switch 105 (a lowermost portion thereof) is located a first axial distance D1 from the bottom end 119 of the handle portion 101 of the electric toothbrush handle 100. Furthermore, when the cap 140 is in the protective state and mounted to the electric toothbrush handle 100, the bottom edge 145 of the tubular sidewall 141 of the cap 140 is located a second axial distance D2 from the bottom end 119 of the handle portion 101 of the electric toothbrush handle 100. Furthermore, in the exemplified embodiment the transverse step 104 of the handle portion 101 is located a third axial distance D3 from the bottom end 119 of the handle portion 101 of the electric toothbrush handle 100. Moreover, the free end 151 of the protective member 150 of the cap 140 is located a fourth axial distance D4 from the bottom end 119 of the handle portion 101 of the electric toothbrush. The status indicator element 171 on the handle portion 101 is located a fifth distance D5 from the bottom end 119 of the handle portion 101 of the electric toothbrush. In the exemplified embodiment, the second axial distance D2 is greater than the first axial distance D1 and the third axial distance D3 is greater than the second axial distance D2. Furthermore, in the exemplified embodiment the fourth axial distance D4 is less than the first axial distance D1, although in other embodiments the fourth axial distance D4 may be substantially the same as the first axial distance D1. Thus, in the exemplified embodiment the free end 151 of the protective member 150 is located closer to the bottom end 119 of the handle portion 101 than a lower most portion of the user actuatable power switch 105. This facilitates the protective member 150 overlying, covering and protecting the user actuatable power switch 105. Furthermore, in the exemplified embodiment the fifth axial distance D5 is less than the first and fourth axial distances D1 and D4, respectively. This prevents the free end 151 of the protective member 150 from overlying or covering the status indicator element 171 so that the status of the electric toothbrush can readily be viewed by the user even when the protective member 150 is coupled to the handle portion 101.

In the exemplified embodiment, the tubular sidewall 141 comprises an engagement portion 165 extending between the transverse shoulder 148 and the bottom edge 145 of the tubular sidewall 141. More specifically, the engagement portion 165 comprises the entire portion of the tubular sidewall 141 extending beneath the transverse shoulder 148 such that the engagement portion 165 comprises the bottom edge 145. As illustrated in FIG. 3, when the cap 140 is in the protective state, the engagement portion 165 of the cap 140 is in surface contact with an engagement portion 166 of the handle portion 101. Furthermore, when the cap 140 is in the protective state, a lower portion 170 of the handle portion 101 remains exposed. Thus, when the cap 140 is in the protective state, the lower portion 170 of the handle portion 101 is not located within the cavity 144 of the cap 140, but rather is exposed for direct gripping by a user.

Figure 13:
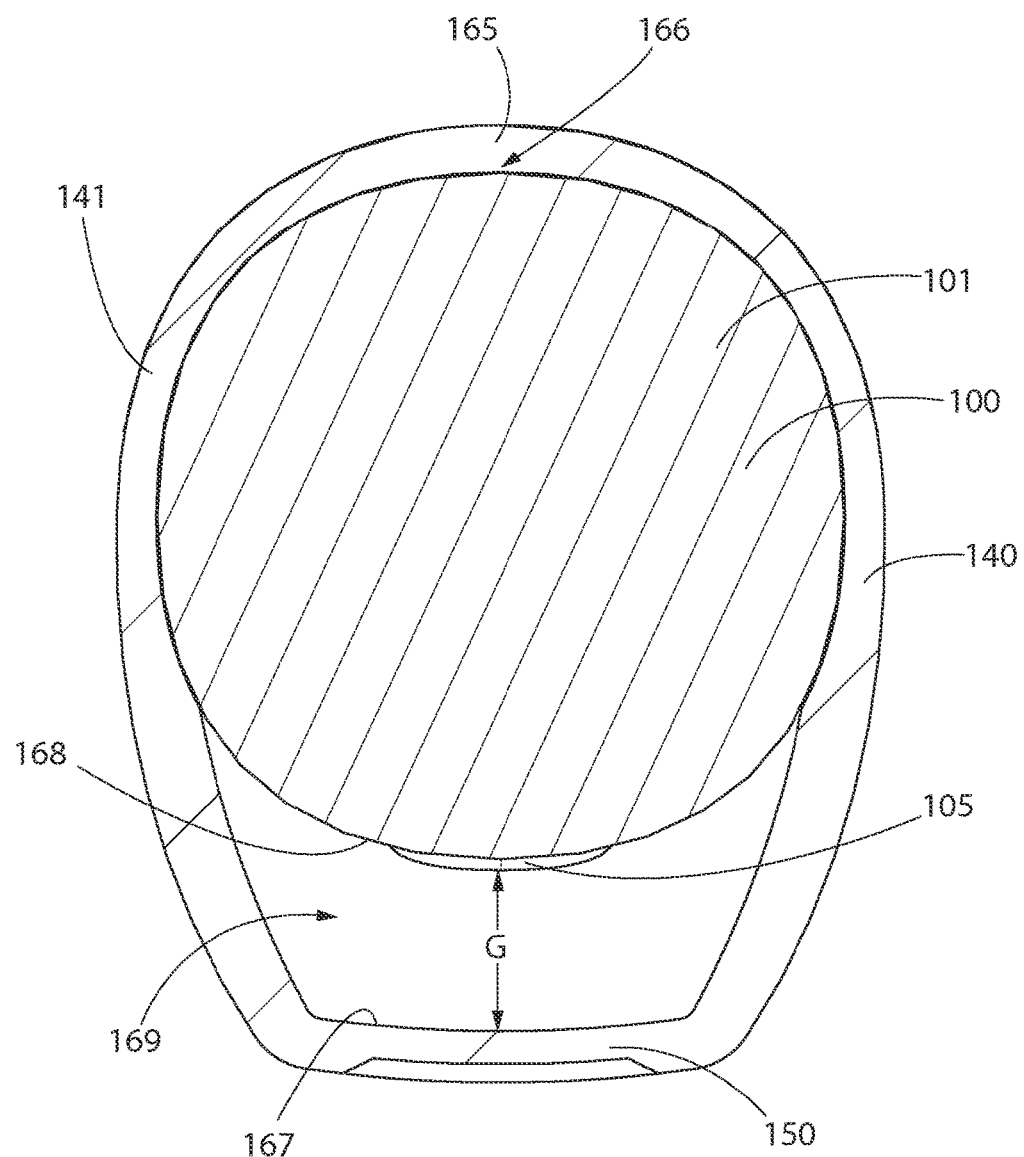
FIG. 13 is a cross-sectional view taken along line XIII-XIII of FIG. 3.
Figure 14:
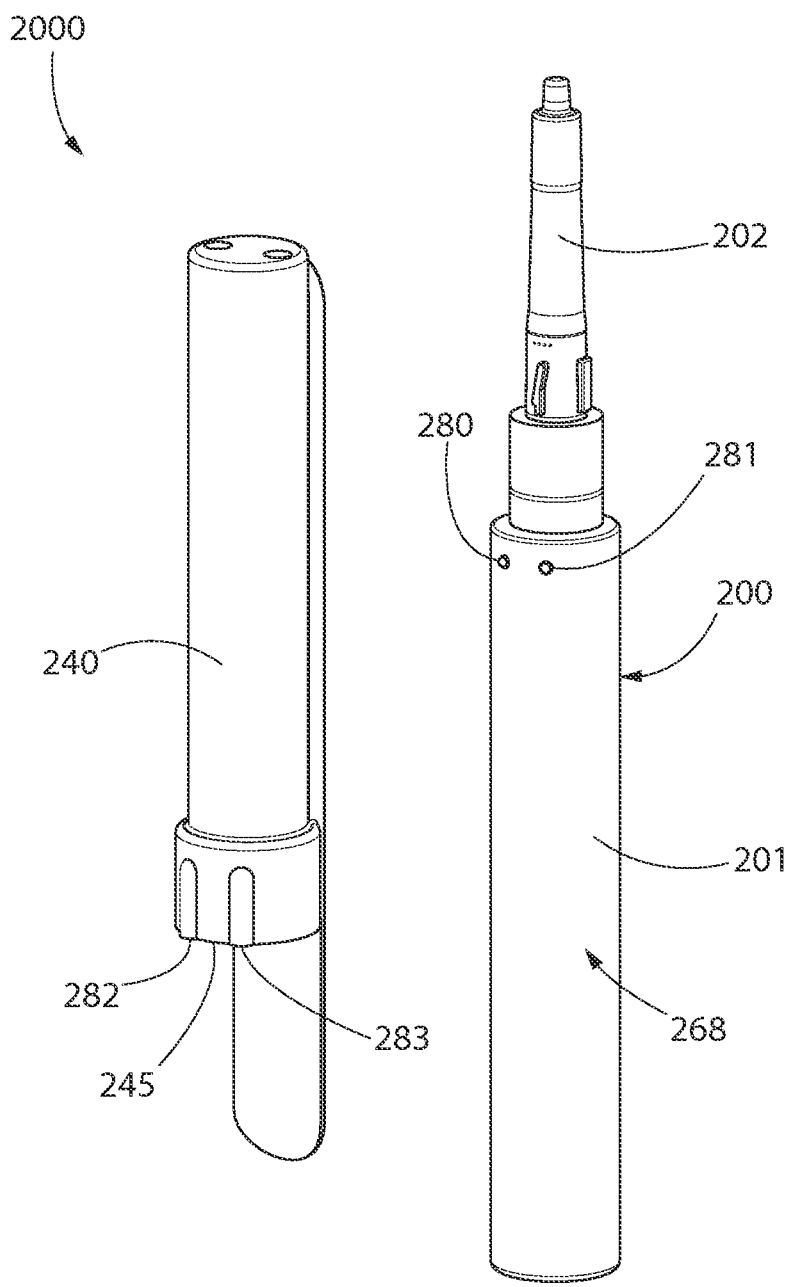
FIG. 14 is a rear perspective view of an electric toothbrush apparatus including an electric toothbrush handle and a cap in an exploded state in accordance with a second embodiment of the present invention.
Figure 15:
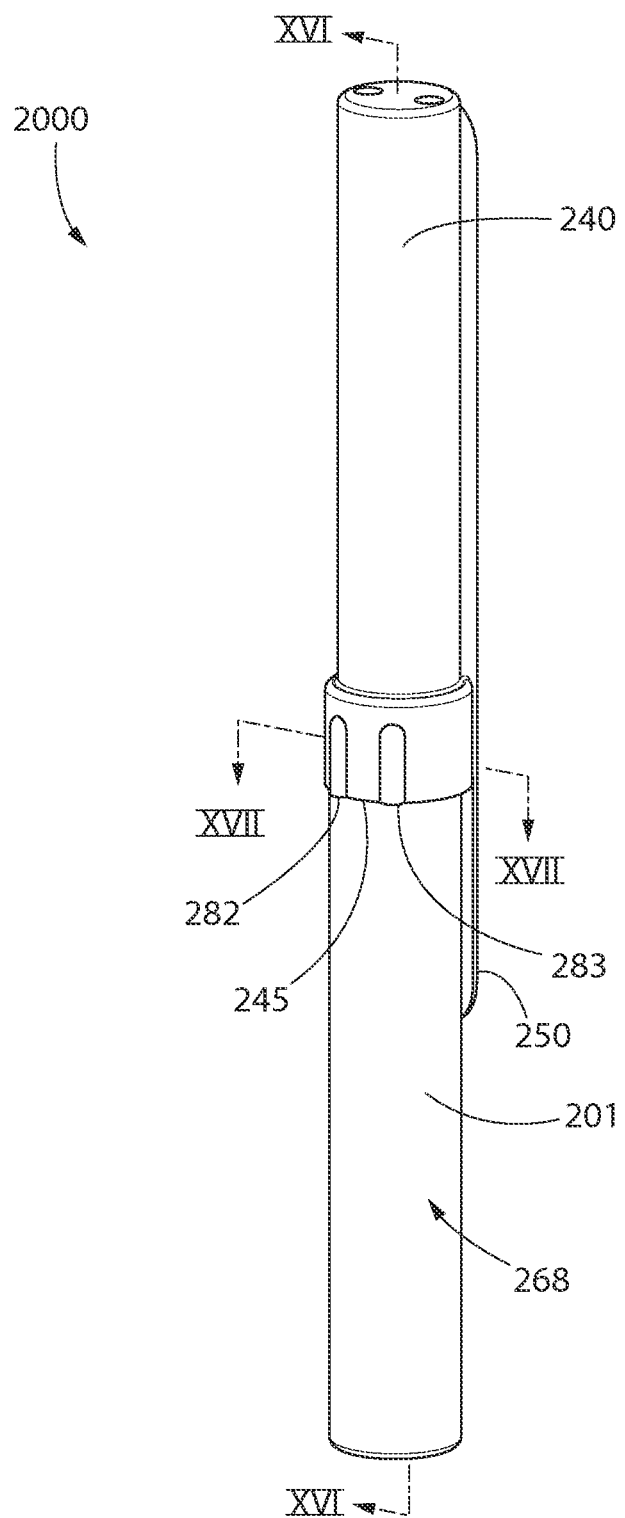
FIG. 15 is a rear perspective view of the electric toothbrush apparatus of FIG. 14 in an assembled state.
Figure 16:
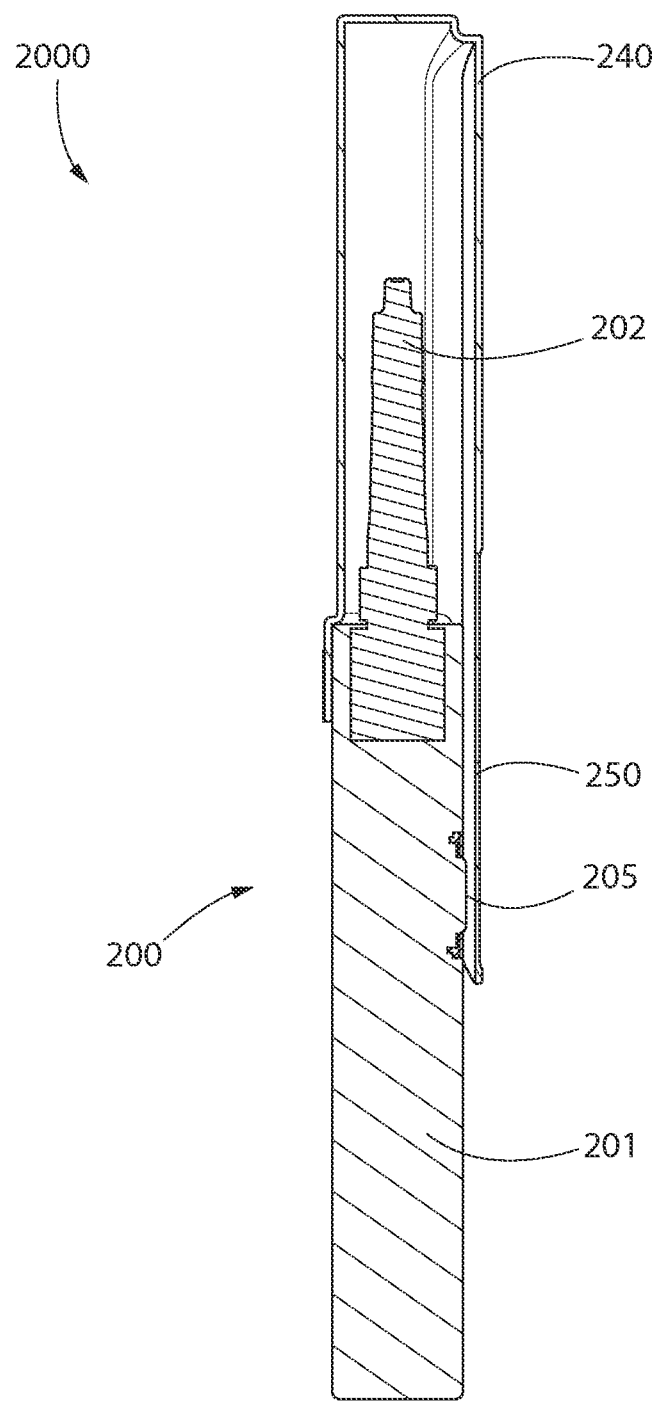
FIG. 16 is a cross-sectional view taken along line XVI-XVI of FIG. 15.
Figure 17:
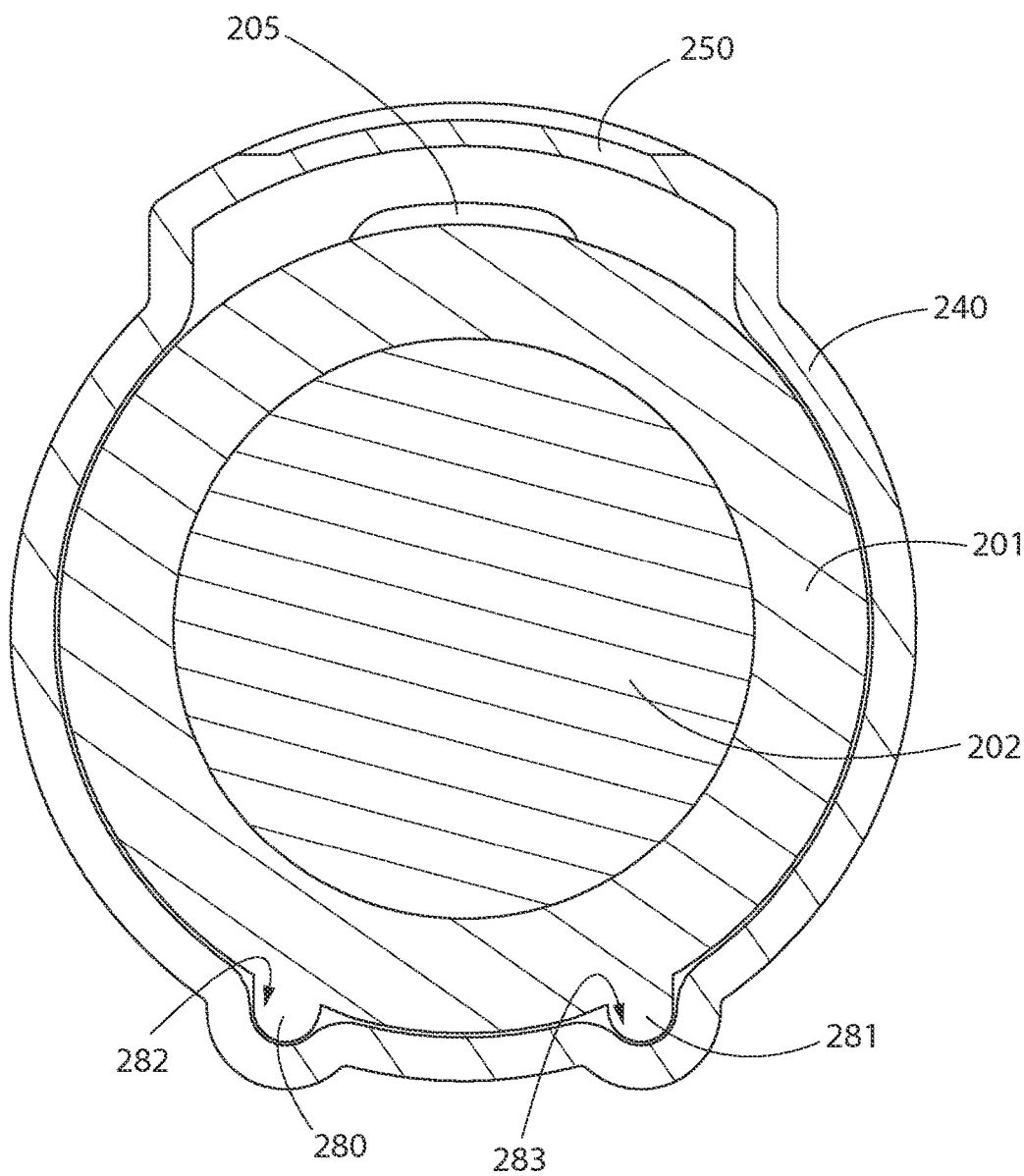
FIG. 17 is a cross-sectional view taken along line XVII-XVII of FIG. 15.

Referring briefly to FIG. 13, the structure and shape of the engagement portion 165 of the tubular sidewall 141 and the engagement portion 166 of the handle portion 101 will be discussed in more detail. The engagement portions 165, 166 of the tubular sidewall 141 and the handle portion 101 include the entirety of the tubular sidewall 141 and the handle portion 101 that are in surface contact with one another when the cap 140 is mounted on the electric toothbrush handle 100. In the exemplified embodiment, the engagement portions 165, 166 encompass greater than 180° of the circumference of each of the tubular sidewall 141 and the handle portion 101, and more specifically between 180° and 270° of the circumference of each of the tubular sidewall 141 and the handle portion 101.

In the exemplified embodiment the engagement portions 165, 166 of the tubular sidewall 141 and the handle portion 101 have non-circular transverse cross-sections. More specifically, in the exemplified embodiment the engagement portions 165, 166 of the tubular sidewall 141 and the handle portion 101 have oval-shaped transverse cross-sections, although in other embodiments the engagement portions 165, 166 of the tubular sidewall 141 and the handle portion 101 may have other shaped transverse cross-sections such as triangular, square, rectangular, or any other polygonal shape. As a result of the non-circular transverse cross sections for the engagement portions 165, 166, the surface contact between the engagement portions 165, 166 of the tubular sidewall 141 and the handle portion 101 prevents relative rotation between the electric toothbrush handle 100 and the cap 140 when the cap 140 is in the protective state. Furthermore forming the engagement portions 165, 166 of the tubular sidewall 141 and the handle portion 101 with non-circular transverse cross-sections facilitates proper alignment between the cap 140 and the electric toothbrush handle 100. Of course, the invention is not to be so limited and in other embodiments the engagement portions 165, 166 of the tubular sidewall 141 and the handle portion 101 may have circular transverse cross-sections to enable rotation between the electric toothbrush handle 100 and the cap 140. Furthermore, when alignment and anti-rotation is desirable, other features can be used to achieve that goal, one particular embodiment of which will be described in detail below with reference to FIGS. 14-17.

Referring now to FIGS. 3 and 13 concurrently, the electric toothbrush apparatus 1000 will be further described. The protective member 150 comprises an inner surface 167 and the handle portion 101 of the electric toothbrush handle 100 comprises an outer surface 168. The inner surface 167 of the protective member 150 is spaced apart from the outer surface 168 of the handle portion 101 of the electric toothbrush handle 100. Furthermore, the inner surface 167 of the protective member 150 is spaced apart from the user actuatable power switch 105 by a gap G. Thus, the protective member 150 is not in surface contact with the user actuatable power switch 105, which further facilitates ensuring that the user actuatable power switch 105 is not accidentally depressed. Furthermore, although the protective member 150 is a flat plate that is cantilevered from the bottom edge 145 of the tubular sidewall 141, the cap 140 is formed of a substantially rigid material so that the protective member 150 cannot easily be pressed into contact with the user actuatable power switch 105. Of course, if a user applies substantial force against the protective member 150 in the direction of the gap G, the protective member 150 may in some embodiments be capable of contacting the user actuatable power switch 105. However, during normal handling the protective member 150 will be pressed into surface contact with the user actuatable power switch 105.

In certain embodiments, the inner surface 167 of the protection member 150 may be contoured or arcuate or rounded in shape. Furthermore, a perimetric edge (or portions thereof) of the protection member 150 may be in contact with the outer surface 168 of the handle portion 101. At the same time, the inner surface 167 of the protection member 150 may be spaced apart from the outer surface 168 of the handle portion 101 and from the user actuatable power switch 105. As a result, the portions of the perimetric edge of the protection member 150 that are in contact with the outer surface 168 of the handle portion 101 will prevent the protection member 150 from coming into direct contact with the user actuatable power switch 105, thereby preventing accidental actuation of the user actuatable power switch 105. In this regard, the protection member 150 may include a pocket or recess region for accommodating the user actuatable power switch 105 to ensure no contact between the protection member 150 and the user actuatable power switch 105 occurs. In certain embodiments the outer edge of the protection member 150 along the lateral sides thereof may contact the outer surface 168 of the handle portion 101 while the outer edge of the protection member 150 along the free end 151 thereof may be spaced apart from the outer surface 168 of the handle portion 101. This will enable the formation of a second passageway, discussed in more detail below, while also increasing the protection of the user actuatable power switch 105.

Furthermore, in the exemplified embodiment the free end 151 of the protective member 150 is spaced apart from the outer surface 168 of the handle portion 101 of the electric toothbrush handle 100 and from the user actuatable power switch 105. As a result of the free end 151 of the protective member 150 being spaced apart from the outer surface 168 of the handle portion 101 and from the user actuatable power switch 105, a second passageway 169 is formed. The second passageway 169 enables air in the environment external to the electric toothbrush apparatus (i.e., an ambient atmosphere) to enter into the gap G and into the cavity 144 of the cap 140. This can assist in the toothbrush head 120 drying out after use and preventing the growth of contaminants. The combination of the second passageway 169, the gap G, the cavity 144 and the holes 127 enable air to passively flow through the cavity to dry the tooth cleaning elements 123 of the toothbrush head 120. In the exemplified embodiment, the second passageway 169 is created from the external environment into the cavity 144 because no portion of the inner surface 167 of the protective member 150 is in contact with either the outer surface 168 of the handle portion 101 or the user actuatable power switch 105.

As noted above, in the exemplified embodiment the protective member 150 is a cantilevered extension of the tubular sidewall 141 of the cap 140. However, in other embodiments the protective member may be formed as a part of the tubular sidewall 141 of the cap 140 such that the bottom edge 145 of the tubular sidewall 141 is an annular edge and no structures protrude beyond the bottom edge 145 of the tubular sidewall 141. In such an embodiment, the protective member portion of the tubular sidewall 141 will be spaced apart from the outer surface 168 of the handle portion and from the user actuatable power switch 105 so that the second passageway 169 and the gap G remains as discussed above.

Referring now to FIGS. 14-17 concurrently, an electric toothbrush apparatus 2000 will be described in accordance with an alternative embodiment of the present invention. The electric toothbrush apparatus 2000 is similar to the electric toothbrush apparatus 1000 in many respects, and thus similar features will be similarly numbered except that the 200-series of numbers will be used. Certain features of the electric toothbrush apparatus 2000 may be similarly numbered as the electric toothbrush apparatus 1000 but might not be described in detail herein in the interest of brevity, it being understood that the discussion of the similar component on the electric toothbrush apparatus 1000 applies. Furthermore, features of the electric toothbrush apparatus 1000 described above that are not illustrated on the electric toothbrush apparatus 2000 or that are illustrated and not numbered on the electric toothbrush apparatus 2000 are applicable to the electric toothbrush apparatus 2000 in certain embodiments and vice versa. Thus, various combinations of the description below with regard to the electric toothbrush apparatus 2000 and the description above with regard to the electric toothbrush apparatus 1000 are within the scope of the present invention in some embodiments.

The electric toothbrush apparatus 2000 generally comprises an electric toothbrush handle 200 having a handle portion 201 and a stem portion 201 and a cap 240. Furthermore, although not illustrated, the electric toothbrush apparatus 2000 also includes a toothbrush head that is couplable to the electric toothbrush handle 200. The electric toothbrush handle 200 is similar to the electric toothbrush handle 100 except for the differences noted herein below.

Specifically, the handle portion 201 of the electric toothbrush handle 200 comprises a first protuberance 280 and a second protuberance 281 extending from the outer surface 268 of the handle portion 201. Although two protuberances 280, 281 are illustrated in the exemplified embodiment, in other embodiments a single protuberance may be used or more than two protuberances may be used. The first and second protuberances 280, 281 are circumferentially spaced apart from one another along the outer surface 268 of the handle portion 201. Furthermore, in the exemplified embodiment the first and second protuberances 280, 281 are transversely aligned with one another, although the invention is not to be so limited in all embodiments. The first and second protuberances 280, 281 facilitate alignment of the cap 240 with the electric toothbrush handle 200 and prevent rotation of the cap 240 with the electric toothbrush handle 200 when the cap 240 is in the protective state and coupled to the electric toothbrush handle 200.

For cooperation with the first and second protuberances 280, 281 of the handle portion 201 of the electric toothbrush handle 200, the cap 240 comprises a first recess or groove 282 and a second recess or groove 283. Although two grooves 282, 283 are illustrated in the exemplified embodiment, in other embodiments a single groove or more than two grooves may be used. It is desirable in certain embodiments that the number of grooves be equal to the number of protuberances. The first and second grooves 282, 283 are circumferentially spaced apart from one another along the outer surface of the cap 240. Furthermore, in the exemplified embodiment the first and second grooves 282, 283 are transversely aligned with one another, although the invention is not to be so limited in all embodiments. The cooperation between the first protuberance 280 and the first groove 282 and the second protuberance 281 and the second groove 283 prevents rotation of the cap 240 relative to the electric toothbrush handle 200 and facilitates proper alignment of the cap 240 with the electric toothbrush handle 200.

In the exemplified embodiment, each of the first and second grooves 282, 283 is formed into an inner surface of a portion of the outer surface of the cap 240 that protrudes outwardly from the remainder of the outer surface of the cap 240. Of course, the invention is not to be so limited and in other embodiments the first and second grooves 282, 283 may simply be indents formed into the inner surface of the cap 240 without requiring a portion of the outer surface of the cap 240 to protrude outwardly. However, having the outwardly protruding portion of the cap 240 facilitates properly aligning the grooves 282, 283 with the protuberances 280, 281 of the handle portion 201.

When it is desired to couple the cap 240 to the electric toothbrush handle 200, the cap 240 is positioned onto the electric toothbrush handle 200 so that the first groove 282 is axially aligned with the first protuberance 280 and the second groove 283 is axially aligned with the second protuberance 281. Then, as the cap 240 is slid axially downwardly onto the electric toothbrush handle 200, the first protuberance 280 enters into the first groove 282 and the second protuberance 281 enters into the second groove 283. Once the first protuberance 280 is positioned within the first groove 282 and the second protuberance 281 is positioned within the second groove 283, relative rotation between the cap 240 and the electric toothbrush handle 200 is prevented. If a user attempts to position the cap 240 onto the electric toothbrush handle 200 without the protuberances 280, 281 being aligned with the grooves 282, 283, the bottom edge 245 of the cap 240 will abut against the first and second protuberances 280, 281, thereby preventing the cap 240 from being fully coupled to the electric toothbrush handle 200. In the exemplified embodiment, proper alignment as noted above is required in order to facilitate coupling of the cap 240 to the electric toothbrush handle 200.

Although the invention is described herein with regard to first and second protuberances 280, 281 being positioned on the handle portion 201 and first and second grooves 282, 283 being positioned on the cap 240, the invention is not to be so limited in all embodiments. In certain other embodiments the protuberances can be positioned on the cap 240 and the grooves can be formed into the handle portion 201. Furthermore, other structural arrangements are also possible to facilitate alignment of the cap 240 with the electric toothbrush handle 200 and anti-rotation of the cap 240 relative to the electric toothbrush handle 200. Specifically, other alignment and anti-rotation features can be incorporated into the electric toothbrush apparatuses 1000, 2000 as desired.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An electric toothbrush apparatus comprising:
   an electric toothbrush handle extending along a handle axis, the electric toothbrush handle comprising:
   a handle portion comprising a user actuatable power switch;
   a stem portion axially protruding from the handle portion, the stem portion configured to couple a replaceable toothbrush head to the electric toothbrush handle;
   a power source; and
   a motion inducing assembly;

a cap comprising:
- a tubular sidewall forming a cavity about a cap axis, the cavity having an open bottom end; and
- a protective member axially extending from a bottom edge of the tubular sidewall in a cantilevered manner; and the cap detachably coupled to the electric toothbrush handle so as to be alterable between: (1) a protective state in which the cap is mounted to the electric toothbrush handle such that the stem portion is located within the cavity and the protective member overlies the user actuatable power switch; and (2) a use state in which the cap is removed from the electric toothbrush handle;

wherein the user actuatable power switch is located a first axial distance from a bottom end of the handle portion; and wherein when the cap is in the protective state, the bottom edge of the tubular sidewall is located a second axial distance from the bottom end of the handle portion, the second axial distance being greater than the first axial distance.

2. The electric toothbrush apparatus according to claim 1 wherein the cap further comprises an upper wall enclosing a top end of the cavity.

3. The electric toothbrush apparatus according to claim 1 wherein the stem portion axially protrudes from a top end of the handle portion, the top end of the handle portion comprising a transverse step.

4. The electric toothbrush apparatus according to claim 3 wherein the tubular sidewall comprises an inner surface that at least partially defines the cavity, the inner surface of the tubular sidewall comprising a transverse shoulder; and wherein when the cap is in the protective state, the transverse shoulder of the tubular sidewall abuts the transverse step of the handle portion.

5. The electric toothbrush apparatus according to claim 4 wherein the transverse step is located a third axial distance from the bottom end of the handle portion, the third axial distance being greater than the second axial distance, the second axial distance defined from the bottom end of the handle portion to the bottom edge of the tubular sidewall.

6. The electric toothbrush apparatus according to claim 1 further comprising a gap formed between an inner surface of the protective member and the user actuatable power switch.

7. The electric toothbrush apparatus according to claim 1 wherein the tubular sidewall comprises an engagement portion that comprises the bottom edge; and wherein when the cap is in the protective state, the engagement portion is in surface contact with an engagement portion of the handle portion.

8. The electric toothbrush apparatus according to claim 7 wherein the engagement portions of the tubular sidewall and the handle portion have non-circular transverse cross-sections such that the surface contact between the engagement portions of the tubular sidewall and the handle portion prevents relative rotation between the electric toothbrush handle and the cap when the cap is in the protective state.

9. The electric toothbrush apparatus according to claim 1 wherein a lower portion of the handle portion remains exposed when the cap is in the protective state.

10. The electric toothbrush apparatus according to claim 1 further comprising a replaceable toothbrush head coupled to the stem portion of the electric toothbrush handle; and wherein the replaceable toothbrush head is located within the cavity when the cap is in the protective state.

11. The electric toothbrush apparatus according to claim 10 wherein the replaceable toothbrush head comprises a sleeve portion comprising a sleeve cavity having an open bottom end, a head portion comprising a plurality of tooth cleaning elements, the head portion coupled to a distal end of the sleeve portion, and the stem portion of the electric toothbrush handle disposed within the sleeve cavity.

12. The electric toothbrush apparatus according to claim 1 wherein the protective member terminates in a free end, the free end of the protective member being located closer to the bottom end of the handle portion than a lowermost portion of the user actuatable power switch.

13. The electric toothbrush apparatus according to claim 1 wherein the handle portion comprises a status indicator element, and wherein the protective member terminates in a free end, the status indicator element being located closer to the bottom end of the handle portion than the free end of the protective member.

14. An electric toothbrush apparatus comprising:
an electric toothbrush handle extending along a handle axis, the electric toothbrush handle comprising:
- a handle portion comprising a user actuatable power switch;
- a stem portion axially protruding from the handle portion, the stem portion configured to couple a replaceable toothbrush head to the electric toothbrush handle;
- a power source; and
- a motion inducing assembly;
a cap comprising:
- a tubular sidewall forming a cavity about a cap axis, the cavity having an open bottom end; and
- a protective member axially extending from a bottom edge of the tubular sidewall in a cantilevered manner; and the cap detachably coupled to the electric toothbrush handle so as to be alterable between: (1) a protective state in which the cap is mounted to the electric toothbrush handle such that the stem portion is located within the cavity and the protective member overlies the user actuatable power switch; and (2) a use state in which the cap is removed from the electric toothbrush handle;

wherein the protective member comprises a flat plate.

15. An electric toothbrush apparatus comprising:
an electric toothbrush handle extending along a handle axis, the electric toothbrush handle comprising:
- a handle portion comprising user actuatable input means;
- a toothbrush head coupled to the electric toothbrush handle;
- a power source; and
- a motion inducing assembly;
a cap detachably coupled to the electric toothbrush handle, the cap comprising:
- a tubular sidewall forming a cavity about a cap axis, the cavity having an open bottom end, the toothbrush head located within the cavity; and
- a protective member axially extending from a bottom edge of the tubular sidewall in a cantilevered manner, the protective member overlying the user actuatable input means to prevent actuation thereof;

wherein the user actuatable input means is located a first axial distance from a bottom end of the handle portion; and wherein when the cap is coupled to the electric toothbrush handle, the bottom edge of the tubular sidewall is located a second axial distance from the bottom end of the handle portion, the second axial distance being greater than the first axial distance.

16. The electric toothbrush apparatus according to claim 15 further comprising:
a gap formed between an inner surface of the protective member and the user actuatable input means; and
wherein the protective member terminates at a free end that is spaced apart from an outer surface of the handle portion thereby forming a passageway into the gap.

17. An electric toothbrush apparatus comprising:
an electric toothbrush handle extending along a handle axis, the electric toothbrush handle comprising:
a handle portion comprising user actuatable input means;
a toothbrush head having cleaning elements thereon coupled to the handle portion;
a power source; and
a motion inducing assembly;
a cap detachably coupled to the electric toothbrush handle, the cap comprising:
a sidewall having an inner surface that forms a cavity having an open bottom end and a closed top end, the toothbrush head positioned within the cavity;
a hole forming a first passageway from an ambient atmosphere to a top portion of the cavity; and
a protective member axially extending from a bottom edge of the sidewall in a cantilevered manner; and
a second passageway extending from the ambient atmosphere to a bottom portion of the cavity;
wherein the protective member comprises a flat plate.

18. The electric toothbrush apparatus according to claim 17 wherein the second passageway is formed between an outer surface of the handle portion and a protective member of the cap that extends from a bottom edge of the sidewall in a cantilevered manner, wherein the protective member overlies the user actuatable input means.

* * * * *